United States Patent
Tov

(10) Patent No.: US 10,960,062 B2
(45) Date of Patent: Mar. 30, 2021

(54) METHODS AND USES OF ALPHA 1-ANTITRYPSIN FOR EARLY INTERVENTION IN PULMONARY DISEASES

(71) Applicant: KAMADA LTD., Rehovot (IL)

(72) Inventor: Naveh Tov, Haifa (IL)

(73) Assignee: KAMADA LTD., Rehovot (IL)

( * ) Notice: Subject to any disclaimer, the term of this patent is extended or adjusted under 35 U.S.C. 154(b) by 0 days.

(21) Appl. No.: 16/487,214

(22) PCT Filed: Feb. 21, 2018

(86) PCT No.: PCT/IL2018/050194
§ 371 (c)(1),
(2) Date: Aug. 20, 2019

(87) PCT Pub. No.: WO2018/154568
PCT Pub. Date: Aug. 30, 2018

(65) Prior Publication Data
US 2020/0009234 A1    Jan. 9, 2020

Related U.S. Application Data

(60) Provisional application No. 62/461,231, filed on Feb. 21, 2017.

(51) Int. Cl.
*A61K 38/57* (2006.01)
*A61P 11/00* (2006.01)
*A61K 9/00* (2006.01)

(52) U.S. Cl.
CPC ............ *A61K 38/57* (2013.01); *A61K 9/0073* (2013.01); *A61P 11/00* (2018.01)

(58) Field of Classification Search
CPC .... A61K 38/57; A61K 9/0073; A61K 9/0043; A61P 11/00; A61P 11/06
See application file for complete search history.

(56) References Cited

U.S. PATENT DOCUMENTS

| | | | | |
|---|---|---|---|---|
| 7,638,679 B2* | 12/2009 | Paliard | ............... | C12N 15/8509 800/21 |
| 7,973,005 B2* | 7/2011 | Bauer | ............... | A61K 9/0078 514/1 |
| 8,980,574 B2* | 3/2015 | Crapo | ............... | A61K 9/0019 435/23 |
| 9,457,070 B2* | 10/2016 | Dinarello | ............... | A61P 37/06 |
| 9,486,509 B2* | 11/2016 | Gottlieb | ............... | A61K 39/001 |
| 9,522,179 B2* | 12/2016 | Dinarello | ............... | A61K 38/57 |
| 9,938,353 B2* | 4/2018 | Dinarello | ............... | A61P 13/08 |
| 10,450,384 B2* | 10/2019 | Dinarello | ............... | A61P 43/00 |
| 2008/0312136 A1* | 12/2008 | Durrani | ............... | A61K 9/0078 514/1.1 |
| 2015/0011460 A1 | 1/2015 | Forshag et al. | | |
| 2017/0239289 A1* | 8/2017 | Av-Gay | ............... | A61P 31/12 |
| 2020/0046815 A1* | 2/2020 | Strauss | ............... | A61K 38/57 |
| 2020/0330565 A1* | 10/2020 | Tov | ............... | A61K 38/57 |

FOREIGN PATENT DOCUMENTS

| | | |
|---|---|---|
| EP | 2 740 487 | 6/2014 |
| IL | 193319 | 3/2012 |
| WO | 2005/027821 A2 | 3/2005 |
| WO | 2005/048985 A2 | 6/2005 |

OTHER PUBLICATIONS

Nishimura et al. Annual Change in Pulmonary Function and Clinical Phenotype in Chronic Obstructive Pulmonary Disease. Am J Respir Crit Care Med, vol. 185, No. 1, pp. 44-52. (Year: 2012).*
Csikesz et al. New Developments in the Assessment of COPD: Early Diagnosis is Key. International Journal of COPD, vol. 9, pp. 277-286. (Year: 2014).*
Sutton et al. Effects of Puberty on Cystic Fibrosis Related Pulmonary Exacerbations in Women Versus Men, Pediatr Pulmonol. Jan. 2014 ; vol. 49, No. 1, pp. 28-35. (Year: 2014).*
Abboud et al. Alpha1-antitrypsin deficiency: aclinical-genetic overview. The Application of Clinical Genetics. vol. 4, pp. 55-65. (Year: 2011).*
Johannessen, A., et al., "Post-Bronchodilator Spirometry Reference Values in Adults and Implications for Disease Management," Am J Respir Crit Care Med., vol. 173, No. 12, pp. 1316-1325 (Mar. 23, 2006).
Prescribing Information for Prolastin-C. Aug. 2016 https://www.prolastin.com/documents/31477834/0/prolastinpi/b436e646-0787-4aad-a3d5-b5e004cc92c6 (Aug. 31, 2016).
Hubbard et al., "Anti-neutrophil-elastase defenses of the lower respiratory tract in alpha 1-antitrypsin deficiency directly augmented with an aerosol of alpha 1-antitrypsin", Annals of Internal Medicine, 1989, vol. 111, No. 3, pp. 206-212.

* cited by examiner

*Primary Examiner* — Marcela M Cordero Garcia
(74) *Attorney, Agent, or Firm* — Wenderoth, Lind & Ponack, L.L.P.

(57) ABSTRACT

The present invention disclosed methods for early intervention and prevention of the progression of pulmonary diseases, by administering alpha 1-antitrypsin (AAT) and particularly by administering AAT by inhalation.

19 Claims, 6 Drawing Sheets

METHODS AND USES OF ALPHA 1-ANTITRYPSIN FOR EARLY INTERVENTION IN PULMONARY DISEASES

FIELD OF THE INVENTION

The present invention relates to methods for early intervention and prevention of the progression of pulmonary diseases by administering alpha 1-antitrypsin (AAT) via inhalation.

BACKGROUND OF THE INVENTION

AAT is a heavily glycosylated plasma protein of 52 kDa in size. AAT is produced by the liver and secreted into the circulation, and is also produced locally by lung epithelial cells. Circulating levels of AAT increase during acute phase response. This increase is due to the presence of IL-1 and IL-6 responsive elements inside the promoter region of the AAT encoding gene. AAT functions as a serine protease inhibitor that primarily targets elastase, trypsin and proteinase-3, three inflammatory and immune cell-derived enzymes that are involved in protease-activated receptor (PAR) activation and the onset and progression of inflammation (Vergnolle N. 2009. Pharmacol Ther 123(3):292-309). Important pro-inflammatory mediators such as IL-1β, IL-6, IL-8 and TNFα are enhanced by these serine proteases and hence blocked by serine protease inhibitors, in particular by AAT (Pott G B et al. 2009. J Leukoc Biol. 85(5):886-95). Moreover, AAT induces the production and release of anti-inflammatory mediators such as IL-10 and IL-1-receptor antagonist (IL-1Ra) (Lewis E C et al. 2008. Proc Natl Acad Sci USA. 105(42):16236-41).

In the lungs, AAT maintains the damage of the airway and alveoli by directly and stoichiometrically inhibiting the activity of neutrophil elastase. In conditions with lower level of AAT (serum level below the normal range 80 mg/dl), there is access of neutrophil elastase that increases breakdown of elastin leading to the airway destruction. This manifest clinically as chronic obstructive pulmonary disease (COPD) with emphysema and chronic bronchitis.

Chronic Obstructive Pulmonary Diseases (COPD)

COPD is a disease state characterized by airflow limitation that is not fully reversible. The airflow limitation is usually progressive and associated with an abnormal inflammatory response of the lung to noxious particles or gases and AAT deficiency is the most prevalent genetic cause accounting for up to 3% of the COPD cases. Symptoms, functional abnormalities and complications of COPD can be attributed to this underlying phenomenon of abnormal inflammatory response and to processes related thereto.

The chronic airflow limitations characteristic of COPD is caused by a mixture of small airway disease (obstructive bronchitis) and parenchymal destruction (emphysema). Usually it developed through years as an asymptomatic process and relative contribution of the bronchitis and emphysema vary from person to person. The chronic inflammation causes remodeling and narrowing of the small airway. Destruction of the lung parenchyma, also by inflammation processes, leads to the loss of alveolar attachments to the small airways and decrease the lung elastic recoil; these changes diminish the ability of the airways to remain open during expiration. In addition to inflammation, two other processes are thought to be important in the pathogenesis of COPD: imbalance of proteinases and anti-proteinases in the lung, and oxidative stress. These processes may themselves be consequences of inflammation, or they may arise from environmental (e.g., oxidant compounds in cigarette smoke) or genetic (e.g. alpha-1 antitrypsin deficiency) factors. In subjects with normal AAT activity, the imbalance may be a consequence of the inflammation induced by inhalational exposure to harmful substances, oxidative stress and possibly other COPD risk factors.

Alpha-1 Antitrypsin Deficiency (AATD)

AATD is an inherited disorder affecting about 1 in 1,500 to 3,500 individuals of European ancestry. Patients with AATD usually have lung damage in early age even before their first symptoms of lung disease between the ages of 20 and 50. These may present as shortness of breath, reduced ability to exercise, or wheezing, and propensity to respiratory infections. The consequence of the low levels of AAT in the lower respiratory tract epithelial lining fluid of individuals with AAT deficiency is an insufficient anti-neutrophil elastase protective screen of the lung, such that a neutrophil elastase is able to act unimpeded to attack and destroy alveolar structures.

Based on the pathology of AAT deficiency an imbalance between proteinases and anti-proteinases results in lung destruction, wherein the imbalance may involve either increased production or activity of proteinases, or inactivation or reduced production of anti-proteinases.

Cystic Fibrosis (CF)

CF is an autosomal recessive, hereditary disease caused by defects in the cystic fibrosis transmembrane conductance regulator (CFTR) gene. The CFTR gene encodes a cAMP-gated channel that is involved in chloride and bicarbonate transport. It regulates sodium transport through inhibition of the epithelial sodium channel, which is encoded by the SCNN1A gene. CFTR is expressed on the apical surface of epithelial cells in the airway, gastrointestinal tract, reproductive tract, sweat glands and submucosal glands. CF affects one in 3,500 children born in the United States. It is the most common fatal autosomal recessive disease in individuals of European descent (Tobias 2011; Essential Medical Genetics, John Wiley & Sons, ed. p. 312). There are approximately 30,000 subjects in the United States with the disease (From the Cystic Fibrosis Foundation; cff. org, accessed on Mar. 19, 2015).

Aberrant chloride and sodium transport due to decreased CFTR activity causes lowered apical surface fluid levels in the lungs, which leads to "sticky" mucous and lower airway obstruction. Subjects having CF or CF-like disease suffer from frequent infections due to inability to clear mucous. Local inflammatory mediators try to clear the infection but have difficulty. The triad of inflammation, infection and obstruction leads to access of neutrophil elastase and other proteases that damage the lung parenchyma progressively since child birth. Eventually, many subjects having CF or CF-like disease suffer from lung disease in early childhood and they die in their late 30's due to respiratory failure.

Treatments for the pulmonary manifestations of CF or CF-like disease include: antibiotics (oral, inhaled and intravenous), CFTR modulators (including CFTR potentiators), DNase, chest physiotherapy to loosen secretions and anti-inflammatory therapeutics. At the end stage, patients may benefit from lung transplant. Current treatments are slowing disease progression but do not reverse the damage to the lungs or cure CF or CF-like disease. Average life expectancy for subjects having CF or CF-like disease had been prolonged in the last 30 years but still they die around 37 years of age (MacKenzie et al., 2014; Annals of Internal Medicine 161(4):233-41). 80% of patients with CF or CF-like disease die from end-stage lung disease.

AAT in aerosolized route has also been proposed as a treatment for cystic fibrosis (CF) patients who suffer from recurrent endobronchial infections and sinusitis. In patients with CF, however, the unregulated inflammatory response overwhelms the normal protease (elastase)/anti-proteinase (AAT) balance. The abnormal cycle is destructively self-perpetuating and leads to the accumulation of elastase in the lung and ultimately to tissue damage, destruction of the lung architecture, severe pulmonary dysfunction and, ultimately, death. Supplemental AAT may reduce the deleterious effects associated with excessive amounts of elastase. It has been recently shown that inhalation of AAT by CF patients increased the AAT levels and decreased elastase activity levels, neutrophils, pro-inflammatory cytokines and numbers of *Pseudomonas*, but had no effect on lung function (Matthias G. et al., ERJ Express. 2006. DOI: 10.1183/09031936.00047306).

International application WO2005/027821 to the applicant of the present invention teaches a novel composition of purified, stable, active alpha-1 antitrypsin (AAT) for intravenous administration and inhalation, a process for its preparation and its use for treating pulmonary disease, including pulmonary emphysema and CF associated lung disease or disorder. The contents of WO2005/027821 are incorporated herein by reference in their entirety.

AAT is currently administered intravenously by using intravenous formulations indicated for augmentation therapy in patients having congenital deficiency of AAT with clinically evident emphysema.

Although the use of augmentation therapy restores physiological levels of AAT to patient's plasma, and may protect the remaining structure of lung parenchyma, serious problems in the disease management still remain. There is still uncertainty of the therapy efficacy, and in addition, there is a limited availability of AAT, particularly as the use of intravenous replacement requires relatively large amounts of the protein. Moreover, it does not provide appropriate means for early intervention and prevention of the progression of pulmonary diseases. Early treatment of pulmonary diseases in the absence of severe symptoms may prevent or delay the irreversible damage.

There is an unmet need for early intervention and prevention of the progression of pulmonary diseases.

SUMMARY OF THE INVENTION

The present invention provides methods for early intervention and prevention of the progression of pulmonary diseases. Particularly, the present invention provides methods for preventing pulmonary diseases, including pulmonary diseases associated with alpha-1 antitrypsin (AAT) deficiency and CF children since the 1$^{st}$ year of life, by administering AAT via inhalation.

The present invention discloses for the first time that pulmonary diseases can be prevented or ameliorated effectively by administering to the lungs of a subject in need thereof a therapeutically effective amount of AAT, particularly by administering the AAT via inhalation. The AAT inhalation can be administered as the sole therapy, or in addition to intravenous AAT augmentation therapy.

The present invention is based in part on the findings that inhaled AAT is an effective and safe preventive therapy for the prevention of lung disease in AAT deficient individuals.

According to the present invention, AAT can be used for delaying the onset or progression of pulmonary disease in a subject in need thereof by the daily administration of an effective amount of inhaled AAT. AAT can be also used for the maintenance of a pulmonary disease-free state by the daily administration of an effective amount of inhaled AAT.

Some embodiments of the present invention concern administration of AAT early or at the onset of the pulmonary disease (early intervention) to prevent or decrease the severity of the disease. Early intervention therapy is unquestioned and patients suffering from chronic obstructive pulmonary diseases would benefit from immediate therapy.

According to one aspect, the present invention provides a method for preventing the progression of pulmonary diseases; the method comprises administering to a subject in need thereof a therapeutically effective amount of alpha 1-antitrypsin (AAT) via inhalation. According to certain embodiments, the pulmonary diseases are selected from the group consisting of alpha 1-antitrypsin deficiency (AATD), small airway disease, chronic bronchitis, emphysema, chronic obstructive pulmonary disease (COPD) with normal level of AAT, cystic fibrosis, bronchiectasis, asthma, pneumonia, parenchymatic and fibrotic lung diseases or disorders, interstitial pulmonary fibrosis and sarcoidosis.

According to certain embodiments, the AAT is aerosolized. According to certain embodiments, the AAT is administered using a nebulizer. According to certain embodiments, the AAT is administered at least once per day. According to certain embodiments, the effective amount of AAT is about 10 mg to about 250 mg AAT per day. According to certain embodiments, the effective amount of AAT is about 80 mg to about 160 mg AAT per day. According to certain embodiments, the effective amount of AAT is about 0.2 mg/kg/day to about 15 mg/kg/day. According to certain embodiments, the AAT is recombinant AAT. According to certain embodiments, the recombinant AAT is inhaled.

According to certain embodiments, the subject is newly diagnosed. According to other embodiments, the subject has lung function measurements of FEV1≥50% of predicted post-bronchodilator. According to certain embodiments, the subject is newly diagnosed by lung densitometry as measured by computed chest tomography.

According to certain embodiments, the subject is selected from the group consisting of a pre-pubertal child, a pre-pubertal adolescent, an adolescent and an adult.

According to some embodiments, the method comprises single dose administration of the total amount of AAT.

According to other embodiments, the method comprises multiple administrations of multiple portion doses to reach the total cumulative dose of AAT. According to certain embodiments, each portion dose comprises from about 15 mg to about 240 mg per day. According to other embodiments, each portion dose comprises 10, 20, 40, 60, 80, 120 or 240 mg AAT/daily. Each possibility represents a separate embodiment of the present invention.

According to certain embodiments, the subject is human.

According to certain embodiments, the method results in: reduced hospitalization; reduced intensive care or mechanical ventilation need; reduced healthcare utilization or burden; reduced absences from school or work; decreased antibiotic need; decreased steroid need; decreased relapse frequency; and decreased morbidity.

Any route of administration as is known in the art to be suitable for AAT administration can be used according to the teachings of the present invention. According to certain embodiments, the AAT is administered via inhalation. The AAT is typically administered within a pharmaceutical composition formulated to complement with the route of administration.

According to additional aspect, the present invention provides a method of preventing or lessening the severity of cystic fibrosis in a pre-pubertal patient in need thereof comprising administering to the pre-pubertal patient a therapeutically effective amount of alpha 1-antitrypsin (AAT) via inhalation. According to some embodiments, the pre-pubertal patient is treated since the first year of life.

According to another aspect, the present invention provides a method of preventing or lessening the severity of alpha 1-antitrypsin deficiency (AATD) in a newly diagnosed subject in need thereof comprising administering to the newly diagnosed subject a therapeutically effective amount of alpha 1-antitrypsin (AAT) via inhalation.

According to certain embodiments, the method comprises early intervention at early stages of diagnosis, even with normal lung function.

According to yet additional aspect, the present invention provides a kit for preventing the progression of pulmonary diseases comprising AAT in a ready to use container or delivery device. According to certain embodiments, the kit, further comprising at least one dose of at least one composition for use in the methods described herein. In certain aspects, for example, the kit comprises at least one daily dose or one effective dose of AAT and a device for delivery of the composition.

Other objects, features and advantages of the present invention will become clear from the following description and drawings.

DETAILED DESCRIPTION OF THE INVENTION

Figure 1:
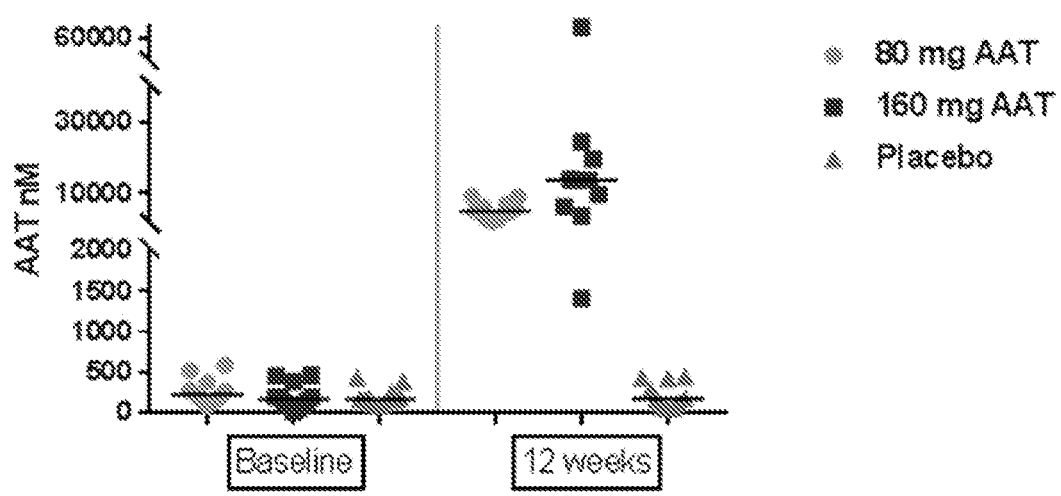
FIG. 1 demonstrates the antigenic AAT in epithelial lining fluid (ELF) according to treatment arm. The black bars mark the median.

The present invention discloses a method for early intervention and preventing the progression of pulmonary diseases; the method comprises administering to a subject in need thereof a therapeutically effective amount of alpha 1-antitrypsin (AAT) via inhalation.

The route of inhalation for the prevention of respiratory diseases has several advantages over other routes of administration, specifically IV administration: Inhalation delivery is directed to the target site, such that there is negligible systemic absorption and side effects are minimized; it requires lower therapeutic doses, and thus there is a greater product availability; it provides quick relief of symptoms and expected good tolerance; it is more convenient form for patients thus better compliance is expected; and it reduces treatment costs as a result of efficient utilization of an expensive drug using stable, purified AAT with a highly efficient nebulizer such as the eFlow.

Definitions

As used herein, the term "Alpha-1 Antitrypsin" (AAT) refers to a glycoprotein that in nature is produced by the liver and lung epithelial cells and secreted into the circulatory system. AAT belongs to the Serine Proteinase Inhibitor (Serpin) family of proteolytic inhibitors. This glycoprotein consists of a single polypeptide chain containing one cysteine residue and 12-13% of the total molecular weight of carbohydrates. AAT has three N-glycosylation sites at asparagine residues 46, 83 and 247, which are occupied by mixtures of complex bi- and triantennary glycans. This gives rise to multiple AAT isoforms, having isoelectric point in the range of 4.0 to 5.0. The glycan monosaccharides include N-acetylglucosamine, mannose, galactose, fucose and sialic acid. AAT serves as a pseudo-substrate for elastase; elastase attacks the reactive center loop of the AAT molecule by cleaving the bond between methionine358-serine359 residues to form an AAT-elastase complex. This complex is rapidly removed from the blood circulation and the lung airways. AAT is also referred to as "alpha-1 Proteinase Inhibitor" (API). The term "glycoprotein" as used herein refers to a protein or peptide covalently linked to a carbohydrate. The carbohydrate may be monomeric or composed of oligosaccharides. It is to be explicitly understood that any AAT as is or will be known in the art, including plasma-derived AAT, recombinant AAT and transgenic AAT can be used according to the teachings of the present invention.

The term "subject," as used herein, refers to any animal, individual, or patient to which the methods described herein are performed. Generally, the subject is human, although as will be appreciated by those in the art, the subject may be an animal. Thus, other animals, including mammals such as rodents (including mice, rats, hamsters and guinea pigs), cats, dogs, rabbits, farm animals including cows, horses, goats, sheep, pigs, etc., and non-human primates (including monkeys, chimpanzees, orangutans and gorillas) are included within the definition of subject.

A "subject in need thereof," as used herein, refers to a subject having or at risk of developing a pulmonary disease. A subject in need thereof may have or be at risk of developing respiratory disease or disorder that is associated with pulmonary disease.

The term "glycoprotein" as used herein refers to a protein or peptide covalently linked to a carbohydrate. The carbohydrate may be monomeric or composed of oligosaccharides.

"Acute" as used herein means arising suddenly and manifesting intense severity. With relation to delivery or exposure, "acute" refers to a relatively short duration.

"Chronic" as used herein means lasting a long time, sometimes also meaning having a low intensity. With regard to delivery or exposure, "chronic" means for a prolonged period or long-term.

As used herein, the terms "exacerbation" "exacerbation period" and "exacerbation episode" are used interchangeably to describe an increase in the severity of symptoms during a course of a disease, which is mostly associated with a worsening of quality of life. Exacerbations are quite frequent in patients with chronic lung diseases in general and in AAT deficient patients in particular. By definition, exacerbations are worsening and/or increase in severity and/or magnitude of the pulmonary disease symptoms.

The terms "prevent" or "preventing" includes alleviating, ameliorating, halting, restraining, slowing, delaying, or reversing the progression, or reducing the severity of pathological conditions described above, or forestalling the onset or development of a disease, disorder, or condition for a period of time from minutes to indefinitely. Prevent also means reducing risk of developing a disease, disorder, or condition.

"Amelioration" or "ameliorate" or "ameliorating" refers to a lessening of at least one indicator, sign, or symptom of an associated disease, disorder, or condition. The severity of indicators may be determined by subjective or objective measures, which are known to those skilled in the art.

The terms "pulmonary delivery" and "respiratory delivery" refer to delivery of AAT to a subject by inhalation/nebulization through the mouth and into the lungs.

"Pulmonary administration" means administration topical to the surface of the respiratory tract. Pulmonary administration includes nebulization, inhalation, or insufflation of powders or aerosols, by mouth and/or nose.

"Inhalation" refers to a method of administration of a compound that delivers an effective amount of the compound so administered or delivered to the tissues of the lungs or lower respiratory tract by inhalation of the compound by the subject, thereby drawing the compound into the lung. As used herein, "administration" is synonymous with "delivery".

The phrases "pulmonary administration," "respiratory administration," "pulmonary delivery," and "respiratory delivery" are synonymous as used herein and refer to the administration and or delivery of AAT to a subject by inhalation through the mouth and or nose and into the lungs and lower respiratory tract.

"Fibrosis" refers to the formation of fibrous tissue. Excess fibrosis in an organ or tissue can lead to a thickening of the affected area and scar formation. Fibrosis can lead to organ or tissue damage and a decrease in the function of the organ or tissue. An example of fibrosis includes, but is not limited to, pulmonary fibrosis (fibrosis of the lung).

As used herein, the terms "cystic fibrosis" or "CF" refer to an inherited autosomal recessive disorder caused by mutations in the gene encoding the cystic fibrosis transmembrane conductance regulator (CFTR) chloride channel.

The term "emphysema," as is used herein, refers to a pathological condition of the lungs in which there is a decrease in respiratory function and often breathlessness due to an abnormal increase in the size of the air spaces, caused by irreversible expansion of the alveoli and/or by the destruction of alveolar walls by neutrophil elastase. Emphysema is a pathological condition of the lungs marked by an abnormal increase in the size of the air spaces, resulting in strenuous breathing and an increased susceptibility to infection. It can be caused by irreversible expansion of the alveoli or by the destruction of alveolar walls. Due to the damage caused to lung tissue, elasticity of the tissue is lost, leading to trapped air in the air sacs and to impairment in the exchange of oxygen and carbon dioxide. In light of the walls breakdown, the airway support is lost, leading to obstruction in the airflow. Emphysema and chronic bronchitis frequently co-exist together to comprise chronic obstructive pulmonary disease.

As used herein, the term "chronic obstructive pulmonary disease" abbreviated "COPD", refers to a disease state characterized by airflow limitation that is not fully reversible. The airflow limitation is usually both progressive and associated with an abnormal inflammatory response of the lungs to noxious particles or gases. COPD is the fourth leading cause of death in America, claiming the lives of 120,000 Americans in 2002, with smoking being a primary risk factor. A diagnosis of COPD exacerbation is considered when there is increases dyspnea, increased sputum volume, and increased sputum purulence. Severity of an exacerbation can be quantified by assessing the magnitude of these three symptoms (Dewan N A 2002. Chest 122:1118-1121).

"Bronchiectasis," as used herein, refers to the abnormal and irreversible dilation of the proximal medium-sized bronchi (>2 mm in diameter) caused by destruction of the muscular and elastic components of the bronchial walls. It can be congenital or acquired. Bronchiectasis can be caused by the bacteria *Streptococcus pneumoniae, Haemophilus influenzae, Staphylococus aureus*, and *Moraxella catarrhalis* and the atypical pneumonias *Legionella pneumoniae, Chlamydia pneumoniae*, and *Mycoplasma pneumoniae* including *Pseudomonas aeruginosa*.

"Asthma," as used herein, refers to a chronic respiratory disease, often arising from an allergy that is characterized by sudden recurring attacks of labored breathing, chest constriction, and coughing. In a typical asthmatic reaction, IgE antibodies predominantly attach to mast cells that lie in the lung interstitium in close association with the bronchioles and small bronchi. An antigen entering the airway will thus react with the mast cell-antibody complex, causing release of several substances, including, but not limited to interleukin cytokines, chemokines, and arachidonic acid-derived mediators, resulting in bronchoconstriction, airway hyperreactivity, excessive mucus secretion, and airway inflammation.

"Pneumonia" as used herein, refers to an acute infection of one or more functional elements of the lung, including alveolar spaces and interstitial tissue. Generally, pneumonia can result from acute lung disease, lung inflammatory disease, or any perturbations in lung function due to factors such as inflammation or coagulation.

"Mycobacterial infection," as used herein, refers to the pulmonary infection caused by various species of *Mycobacterium*. "Tuberculosis" or "TB" is one example of an airborne, chronic *Mycobacterium tuberculosis* infection.

The term "eFlow nebulizer" refers to the nebulizer disclosed in international application WO 01/34232. The term "inhalation nebulizer" refers to a nebulizer comprising the basic elements of the eFlow nebulizer and any equivalent nebulizer. The terms "pulmonary delivery" and "respiratory delivery" refer to delivery of API to a patient by inhalation through the mouth and into the lungs.

The term "dry powder" refers to a powder composition that contains finely dispersed dry particles that are capable of being dispersed in an inhalation device and subsequently inhaled by a subject.

The particles of the dry powder composition have particle size distribution that enables the particles to target the alveolar region of the lung when delivered via inhalation. The particle-size distribution (PSD) of a powder is a list of values or a mathematical function that defines the relative amount of particles present according to size. The powders of the invention are generally polydispersed (i.e., consist of a range of particle sizes). In particular embodiments, the term "particle size distribution" refers to the size distribution of particle system and represents the number of solid particles that fall into each of the various size ranges, given as a percentage of the total solids of all sizes in the sample of interest.

The term "dosage" as used herein refers to the amount, frequency and duration of AAT which is given to a subject during a therapeutic period.

The term "dose" as used herein, refers to an amount of AAT which is given to a subject in a single administration.

The terms "multiple-variable dosage" and "multiple dosage" are used herein interchangeably and include different doses of AAT administration to a subject and/or variable frequency of administration of the AAT for therapeutic treatment. "Multiple dose regimen" or "multiple-variable dose regimen" describe a therapy schedule which is based on administering different amounts of AAT at various time points throughout the course of therapy. In one embodiment, the invention describes a multiple-variable dosage method of treatment.

As used herein the term "about" refers to the designated value ±10%.

The term "simultaneous administration," as used herein, means that the AAT and the additional lung treatment are administered with a time separation of no more than about 15 minute(s), such as no more than about any of 10, 5, or 1 minutes.

"Maintenance therapy" as used herein, refers to the regular, periodic administration of AAT to maintain a sufficient level of A1PI in a subject's lungs or circulatory system to have a therapeutic effect on the subject.

"Augmentation therapy," as used herein, refers to supplementing, replacing, or increasing deficient in vivo quantities or concentrations of a biomolecule, such as AAT, to have a therapeutic effect on a subject.

"Recombinant AAT" as used herein, refers to AAT that is the product of recombinant DNA or transgenic technology. The phrase, "recombinant AAT," also includes functional fragments of AAT, chimeric proteins comprising AAT or functional fragments thereof, fusion proteins or fragments of AAT, homologues obtained by analogous substitution of one or more amino acids of AAT, and species homologues. For example, the gene coding for AAT can be inserted into a mammalian gene encoding a milk whey protein in such a way that the DNA sequence is expressed in the mammary gland as described in, e.g., U.S. Pat. No. 5,322,775, which is herein incorporated by reference for its teaching of a method of producing a proteinaceous compound. "Recombinant AAT," also refers to AAT proteins synthesized chemically by methods known in the art such as, e.g., solid-phase peptide synthesis. Amino acid and nucleotide sequences for AAT and/or production of recombinant AAT are described by, e.g., U.S. Pat. Nos. 4,711,848; 4,732,973; 4,931,373; 5,079,336; 5,134,119; 5,218,091; 6,072,029; and Wright et al., Biotechnology 9: 830 (1991); and Archibald et al., Proc. Natl. Acad. Sci. (USA), 87: 5178 (1990), are each herein incorporated by reference for its teaching of AAT sequences, recombinant AAT, and/or recombinant expression of AAT.

Preparation of AAT

According to one aspect of the present invention a purified stable composition of AAT is provided. Preferably, a liquid composition of purified, stable AAT is provided. International application WO 2005/027821, to the applicant of the present invention, provides pharmaceutical compositions comprising a purified, stable, active AAT in a form of a ready to use sterile solution. WO 2005/027821 also provides process, which combines removal of contaminating substances (i.e., lipids, lipoproteins and other proteins) and separation of active from inactive AAT by sequential chromatography steps. The process disclosed in that invention is highly suitable for a large-scale production of AAT, in the range of tens of kilograms or more. The mixture of proteins from which the AAT is purified is preferably Cohn Fraction IV-1 paste, but can include other Cohn Fractions, separately or in combination; human blood plasma; plasma fractions; or any protein preparation containing AAT. For instance, the process is applicable to purification of recombinant human AAT from the milk of transgenic animals.

In that application, the mixture of proteins comprising AAT is dispersed in an aqueous medium, preferably water, at a ratio of about 13 to about 35 liter per about 1 kg of source material, preferably Cohn Fraction IV-1 paste. The pH of the dispersion is adjusted to a pH range of from about 8.0 to about 9.5. The pH adjustment stabilizes the AAT and promotes the dissolution of the AAT in the dispersion, thereby increasing the production yield. Dispersion may take place at an elevated temperature of between 30° C. and 40° C. for further increase in AAT solubility.

A particular advantage of that process is the elimination of contaminants or by-products that otherwise compromise the efficiency of AAT purification processes. In particular, Cohn Fraction IV-1 paste preparations contain a significant amount of the lipoprotein Apo A-1, which has the effect of compromising column flow and capacity during purification. Other non-desired proteins such as albumin and transferrin are also present in the paste preparation. Removing a portion of such contaminants according to invention disclosed in WO 2005/-27821 is performed by two steps: (a) removing contaminating lipids and lipoproteins by lipid removal agent and (b) precipitating a portion of contaminating protein from the AAT-containing aqueous dispersion. The removal of contaminating proteins, without loss of AAT, enables a significant reduction in equipment scale, e.g., column size.

The precipitate that forms can be separated by conventional means such as centrifugation or filtration, and is then discarded. The supernatant is ready for further purification, for example an anion exchange resin. The AAT is then eluted from the column. The solution is treated to reduce its water content and change the ionic composition by conventional means such as by diafiltration, ultrafiltration, lyophilization, etc., or combinations thereof.

According to one embodiment, the AAT-containing effluent obtained after the first anion exchange chromatography is concentrated by ultrafiltration. The retentate is then diafiltered against pure water to reach conductivity within the range of from about 3.5 to about 4.5 mS/cm.

To further purify the AAT-containing solution obtained after the first anion exchange chromatography the solution is loaded on a cation exchange resin with the same type of buffer used for the anion-exchange step, having appropriate pH and conductivity such to allow the AAT to pass and be washed off with the buffer flow through, while contaminating substances are retained on the cation exchange resin. The AAT-containing solution obtained after the cation exchange chromatography can be treated to reduce its water content. According to one embodiment, the solution is concentrated by ultrafiltration.

The ion-exchange chromatography is also used to separate active AAT from inactive AAT. That invention further comprises methods for separating active AAT from other contaminating substances, including solvent/detergent compounds used for viral inactivation. Such separation is achieved by the second anion exchange chromatography.

The AAT eluted from the second anion exchange chromatography step is therefore not only highly active, but also highly pure. Throughout the process of that invention only one type of buffer is used, with adjustment of pH and conductivity as required throughout the various process steps. According to one embodiment, the buffer is any suitable acid/salt combination that provides acceptable buffer capacity in ranges of pH required throughout the process. According to preferred embodiments the process uses a buffer other than citrate-based buffer. According to yet other embodiments, the buffer anion is acetate. According to one embodiment, the process of that invention further comprises viral removal and/or viral inactivation steps. Methods for viral removal and inactivation are known in the art.

One method for viral removal is filtration, preferably nanofiltration, removing both enveloped and non-enveloped viruses. According to one embodiment, the viral removal step comprises filtration. According to another embodiment, the virus removal step is performed after the cation exchange chromatography. Typically, the cation exchange flow-through solution containing AAT is concentrated, and then nanofiltered. According to one embodiment, the method of viral inactivation employed comprises a solvent/detergent (S/D) treatment. The viral inactivation step is preferably performed prior to loading the solution on the second anion exchange resin. According to one embodiment, the detergent used is polysorbate and the solvent is Tri-n-Butyl-Phosphate (TnBP). According to another embodiment, the polysorbate is polysorbate 80. According to one embodiment Polysorbate 80 may be added from about 0.8% to about 1.3% volume per weight (v/w) of the resulting mixture and TnBP may be added from about 0.2% to about 0.4% weight per weight of the resulting mixture. The solution containing active, purified AAT obtained after the second anion exchange chromatography can be further processed to obtain a pharmaceutical composition for therapeutic, diagnostic, or other uses. To prepare the product for therapeutic administration the process further comprises the steps of changing the ionic composition of the solution containing purified, active AAT to contain a physiologically compatible ion and sterilizing the resulted solution.

The purified AAT obtained by the process of that invention is highly stable. According to one embodiment, the pharmaceutical composition comprises at least 90% pure, preferably 95% pure, more preferably 99% pure AAT. According to another embodiment, at least 90% of the AAT is in its active form.

According to some embodiments, highly dispersible dry powder compositions are used, comprising high concentration of active alpha-1 antitrypsin (AAT) and specific excipients, suitable for pulmonary delivery of AAT. The dry powder compositions disclosed herein comprise according to some embodiments AAT molecules in their monomeric form, having low aggregation level. The AAT dry powder compositions exhibit an exceptional stability and low aggregation properties, and thus are highly suitable for use with inhalation devices as well as in other dry-powder dosage forms.

Pharmaceutical Compositions and Methods of Treatment

The term "pharmaceutical composition" is intended to be used herein in its broader sense to include preparations containing a protein composition in accordance with this invention used for therapeutic purposes. The pharmaceutical composition intended for therapeutic use should contain a therapeutic amount of AAT, i.e., that amount necessary for preventative or curative health measures.

As used herein, the term "therapeutically effective amount" refers to an amount of a protein or protein formulation or composition which is effective to treat a condition in a living organism to which it is administered over some period of time. Pharmaceutical compositions of the present invention may be manufactured by processes well known in the art, e.g. by means of conventional mixing, dissolving, granulating, grinding, pulverizing, dragee-making, levigating, emulsifying, encapsulating, entrapping or lyophilizing processes.

Pharmaceutical compositions for use in accordance with the present invention thus may be formulated in conventional manner using one or more acceptable diluents or carriers comprising excipients and auxiliaries, which facilitate processing of the active compounds into preparations, which can be used pharmaceutically. Proper formulation is dependent on the route of administration chosen. According to certain currently preferred embodiments, the pharmaceutical compositions of the present invention are formulated in a form suitable for inhalation.

The AAT-containing pharmaceutical compositions disclosed in WO2005/027821 to the Applicant of the present invention is advantageous over hitherto known AAT-containing preparations, as the AAT is highly stable also when the composition is kept in a liquid from. Therefore, it is not necessary to lyophilize the AAT preparation for stable storage in a form of a powder. Subsequently, there is no need to reinstate the powder to a liquid before use for parenteral administration or for inhalation. According to certain currently preferred embodiments, AAT in a ready-to-use liquid formulation is used with the methods of the present invention. It has been estimated that only 2% of the intravenously administered AAT dose reaches the lung (Hubbard and Crystal, 1990. Lung 168 Suppl:565-78, 1990). This is a major disadvantage in treating pulmonary diseases in general, and in treating exacerbation episodes in particular.

Therefore, administration of AAT by the inhalation route may be more beneficial as it reaches directly the lower respiratory tract. The inhalation route also requires lower therapeutic doses of AAT and thus the scarce supply of human plasma-derived AAT, currently being the only source for AAT, would be available for the treatment of more patients. This route of administration may be also more effective in neutralizing neutrophil elastase, and in correcting the imbalance between proteinase and anti-proteinases in the lung tissues, and is thus highly suitable for treating pulmonary diseases at periods of exacerbation. In addition, administration by inhalation is simpler and less stressful for the patient than the intravenous route and would reduce the burden on the local health care system (by requiring less clinical input). Formulations of pharmaceutical compositions for administration by the route of inhalation are known in the art, as well as inhaler systems and devices. In general, for administration by inhalation, the active ingredients are delivered in the form of an aerosol spray from a pressurized metered dose inhaler with the use of a suitable propellant, e.g., dichlorodifluoromethane, trichlorofluoromethane, dichloro-tetrafluoroethane or carbon dioxide. The active ingredient in the aerosol spray may be in a powder form administered using a dry powder inhaler, or in aqueous liquid aerosol form using a nebulizer.

Powder inhalers are designed to be used until a given charge of active material is exhausted from the device. The charge loaded into the device will be formulated accordingly to contain the proper inhalation dose amount of AAT for delivery in a single administration. (See generally, Remington's Pharmaceutical Sciences, 18th Ed. 1990, Mack Publishing Co., Easton, Pa., Chapter 92 for information relating to aerosol administration).

Nebulizers for liquid aerosol delivery may be categorized as jet nebulizers operated by a pressurized flow of air using a portable compressor or central air supply in a hospital, ultrasonic nebulizers incorporating a piezo-crystal to provide the energy for generating the aerosol out of an ultrasonic fountain, and electronic nebulizers based on the principle of a perforated vibrating membrane.

Any of a variety of powder inhalers and nebulizers as are known in the art can be used for AAT administration according to the teachings of the present invention. For example, U.S. Pat. No. 6,655,379 discloses methods and devices for delivering an active agent formulation to the lung of a human patient. The active agent formulation may be in dry powder form, it may be nebulized, or it may be in admixture with a propellant. According to the teaching of that patent, the active agent formulation, particularly insulin, is delivered to a patient at an inspiratory flow rate of less than 17 liters per minute.

Methods regarding the delivery of AAT formulations using nebulizers are discussed, for example, in U.S. Pat. Nos. 5,093,316, 5,618,786 and 5,780,440. The Applicant of the present invention and co-workers disclosed the use of eFlow nebulizer, disclosed in International Patent Application WO 01/34232, for AAT delivery to the lung. The eFlow nebulizer provides an increased amount of aerosol during inhalation while minimizing both aerosol losses during exhalation and the residual drug in the nebulizer reservoir. The nebulizer includes an aerosol generator that atomizes the liquid through a vibrating diaphragm into particle sizes that are efficiently delivered to the lungs.

The operating conditions for delivery of a suitable inhalation dose will vary according to the type of mechanical device employed. For some aerosol delivery systems, such as nebulizers, the frequency of administration and operating period will be dictated chiefly by the amount of the active composition (AAT according to the present invention) per unit volume in the aerosol. Typically, the higher the concentration of the protein in the nebulizer solution the shorter is the operating period. Some devices such as metered dose inhalers may produce higher aerosol concentrations than others and thus will be operated for shorter periods to give the desired result. According to certain embodiments, the methods of the present invention employ a nebulizer comprising a ready-to-use inhalation solution comprising therapeutically effective amount of AAT.

According to currently certain preferred embodiments, the ready-to-use liquid pharmaceutical composition is packed in pre-sterilized unit dose vials containing 0.25 ml-10 ml, preferably 0.25 ml to 5 ml, commonly used for ready to use inhalation solutions. The vial can be made of glass or polymeric materials or the liquid can be filled into polyethylene or any other suitable polymer vials, manufactured for instance by a blow fill seal process.

According to other preferred embodiments, at least 60% of the nebulized dose is dissolved in droplets having a diameter of 5 μm or less. Such droplet size enhances the AAT delivery to the alveolar regions, where its activity is mostly required. According to certain embodiments, at least 50%, preferably 60% and more preferably 70% or more of the loaded nominal dose of AAT can be delivered to the subject. According to the teaching of the present invention, AAT is administered at the early stages of various pulmonary diseases. As described hereinabove, the pulmonary disease may be associated with an inherited deficiency in AAT in such case patients typically receive intravenous augmentation therapy of AAT. Thus, according to certain embodiments, the method of the present invention comprises administering to a subject in need thereof a therapeutic amount of AAT via inhalation in combination with administering the AAT intravenously.

Typically, the inhaled AAT is administered for relatively short periods of time. According to certain embodiments, the inhalation time is between about 5-15 minutes, preferably about 10 minutes. The AAT may be administered once a week or administration can be repeated at least twice a week, each day or even twice a day.

The AAT protein is an acute phase reactant protein and, as such, its synthesis is amplified during episodes of inflammation or stress (Sandhaus R A. Alpha 1-Antitrypsin deficiency *6: New and emerging treatments for alpha 1-antitrypsin deficiency. Thorax 59:904-909, 2004), which particularly occurs in exacerbation periods. AAT deficient patients risk severe lung damage during exacerbation periods, due to the inability to mount an effective acute phase AAT elevation. During acute exacerbation periods such shortage of AAT may also occur in normal individuals, resulting in the excess of neutrophil elastase leading to destruction of lung tissues. Addition of a therapeutically significant amount of AAT directly to the lung tissue as disclosed by the present invention satisfies the clinical need for a treatment that provides an adequate answer to the patient's condition and prevents the potential accelerated decline in the disease state due to the exacerbation.

The following examples are presented in order to more fully illustrate some embodiments of the invention. They should, in no way be construed, however, as limiting the broad scope of the invention. One skilled in the art can readily devise many variations and modifications of the principles disclosed herein without departing from the scope of the invention.

EXAMPLES

Example 1: Inhaled Alpha-1-Antitrypsin Restores Lower Respiratory Tract Protease-Anti-Protease Homeostasis and Reduces Inflammation in Alpha-1 Antitrypsin Deficient Individuals This example describes a placebo-controlled, double blind, randomized study of inhaled, nebulized AAT conducted in subjects diagnosed with AAT deficiency.

The aim of this study was to evaluate two different doses of AAT for inhalation on the levels of AAT and other analytes in epithelial lining fluid (ELF) and plasma, and to assess the safety of the treatment in subjects with alpha-1 antitrypsin deficiency (AATD).

Study Design:

Two separate groups of 18 PI ZZ individuals (FEV1≥50%) were evaluated using bronchioalveolar lavage (BAL) before and following 12 weeks of inhaled AAT using a dose of 80 mg once or twice a day (160 mg). The dosing groups where at two separate sites; subjects were randomized in a double blind 2:1 fashion to active AAT or placebo. After 12 weeks subjects received 160 mg of AAT for an additional 12 weeks. Bronchioalveolar lavage (BAL) was performed using 100 ml of saline in 5-20 ml aliquots in 3 separate lobes. The BAL fluid was evaluated separately for all lobes. Comparisons included two separate ways, one as paired lobes (before and after) and total of all 3 lobes. Antineutrophil elastase capacity (ANEC), % polymorphonuclear neutrophils (PMNs), neutrophil elastase (NE), AAT, NE-AAT complex and a panel of inflammatory cytokines were measured and adjusted for the epithelial lining fluid (ELF) volume using the urea method.

Diagnosis and Main Criteria for Inclusion:

The target population for this trial was subjects with documented AAT deficiency (subjects with deficient serum API levels [≤11 µM] who carried deficient disease known mutation, ZZ or Z null only).

Main Inclusion Criteria:

Male or non-pregnant, non-lactating women aged 18-65 years at the time of signature of informed consent.

50% of subjects must not have used AAT inhalation before.

Forced expiratory volume in 1 second (FEV1)≥50% of predicted post-bronchodilator.

No respiratory exacerbations within 6 weeks of baseline.

No signs of chronic and/or acute Hepatitis A, Hepatitis B, Hepatitis C, human immunodeficiency virus (HIV) infection and Parvovirus B19, by nucleic acid testing (NAT) (for Parvovirus B19, NAT result must be <$10^4$ IU/mL).

No significant abnormalities in serum hematology, serum chemistry, serum inflammatory/immunogenic markers and urinalysis according to the Principal Investigator's judgement.

No significant abnormalities in electrocardiogram (ECG) per Investigator judgement.

Not on intravenous (IV) augmentation therapy for at least 8 weeks prior to initial dosing with study drug/placebo and willing to forego IV augmentation therapy for the duration of the study.

Statistical Methods for Study Endpoints:

Stratified Wilcoxon rank-sum test was used to test the difference in change from Visit 2 (baseline) measurements to Visit 6 (Week 12) in selected continuous parameters between 80 mg/day plus 160 mg/day and pooled placebo.

Results:

Compared to placebo, ELF-AAT, ANEC, AAT-NE Complexes concentrations were significantly increased in subjects receiving the 80 mg and 160 mg doses. The average ELF AAT concentrations were 2-5 folds above the normal AAT concentration of 2500 nM found in normal individuals. Paired lobe analysis using the RML demonstrates a significant reduction in % neutrophils and NE in the 80 mg dose group. Pro-inflammatory cytokines were not significantly different in pair lobe analysis. Importantly aerosolized AAT was detected in the plasma of all subjects receiving inhaled AAT in a dose response relationship. All subjects tolerated inhaled AAT and adverse events were very rare.

There was a statistically significant difference between the pooled AAT and placebo groups in the median change from baseline to Week 12 in the levels of antigenic and functional AAT in ELF ($p<0.0001$ for both measurements). Notably, at both dosage levels evaluated (80 mg/day and 160 mg/day), subjects treated with "AAT for Inhalation" demonstrated a significant increase in ELF antigenic and functional AAT levels compared to those on placebo where there was no change in AAT level.

FIG. 1 shows the levels of antigenic AAT in ELF over the study period (median and interquartile range). The median change from baseline to Week 12 in the levels of antigenic AAT in ELF was significantly greater in the AAT group than placebo at 80 mg (estimated difference: 4384.05 nM [95% CI: 2390.3, 6825.5; p=0.0003]) and 160 mg (estimated difference: 13510.70 nM [95% CI: 3541.3, 24578.8; p=0.0007]). The difference in the median change from baseline to Week 12 in ELF antigenic AAT levels was also statistically significant when comparing all three treatment groups (80 mg/day AAT, 160 mg/day AAT and pooled placebo group) ($p<0.0001$, Kruskal-Wallis test).

Figure 2:
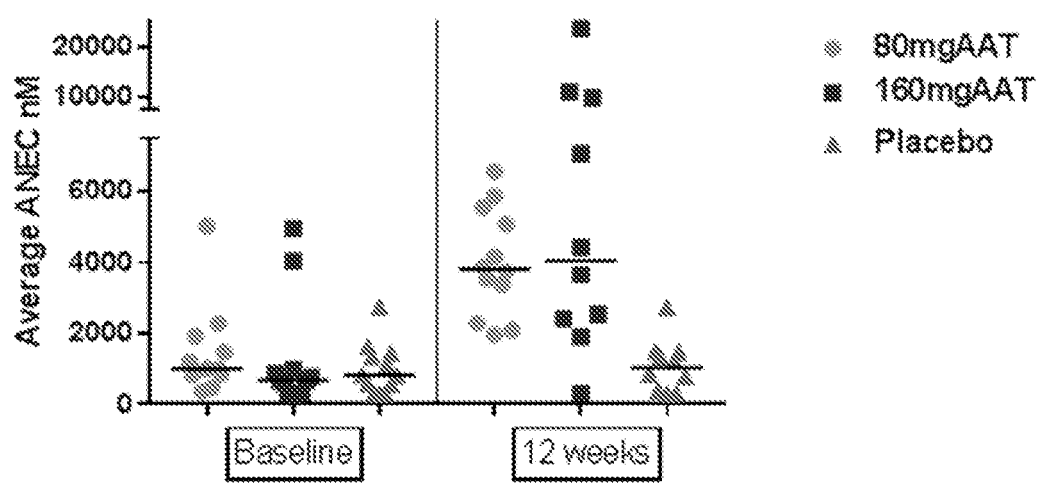
FIG. 2 demonstrates the functional AAT in ELF (average anti-neutrophil elastase capacity (ANEC)) according to treatment arm. The black bars mark the median.

FIG. 2 shows the levels of functional AAT in ELF over the study period (median and interquartile range). The median change from baseline to Week 12 in the levels of functional AAT in ELF was significantly greater in the AAT group than placebo at 80 mg (estimated difference: 2808.57 nM [95% CI: 864.5, 4642.2; p=0.0006]) and 160 mg (estimated difference: 3260.76 nM [95% CI: 698.5, 10004.2; p=0.0193]). The difference in the median change from baseline to Week 12 in ELF functional AAT levels was also statistically significant when comparing all three treatment groups (80 mg/day AAT, 160 mg/day AAT and pooled placebo group) (p=0.0007, Kruskal-Wallis test).

Subjects treated with active drug AAT demonstrated a statistically significant increase in AAT-Neutrophil Elastase (NE) complexes in ELF compared to those on placebo at 80 mg (p=0.0003) and 160 mg (p=0.0007).

Figure 3:
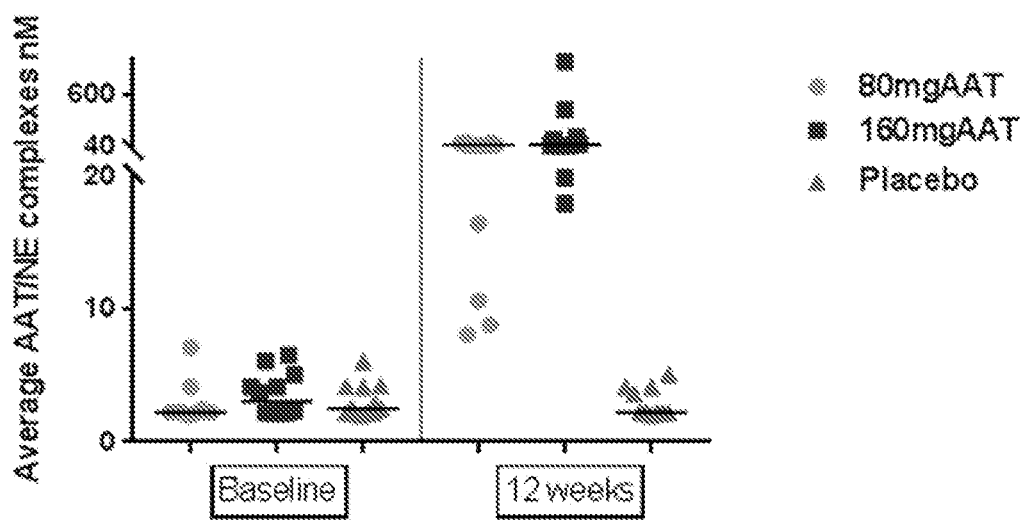
FIG. 3 demonstrates the concentration of AAT/neutrophil elastase (NE) complexes in ELF. The black bars mark the median.

The median change from baseline to Week 12 in the levels of AAT-NE complexes in ELF was significantly greater in the AAT group than placebo at 80 mg (estimated difference: 38.97 nM [95% CI: 8.9, 67.1; p=0.0003]) and 160 mg (estimated difference: 45.93 nM [95% CI: 19.7, 435; p=0.0007]). The difference in the median change from baseline in the levels of AAT-NE complexes in ELF was also statistically significant when comparing all three treatment groups (80 mg/day AAT, 160 mg/day AAT and pooled placebo group) ($p<0.0001$, Kruskal-Wallis test). FIG. 3 shows a graphical representation of the average concentration of AAT-NE complexes in ELF during the double-blind period. There is a significant difference from the baseline and between the placebo and treated groups.

Conclusion: Inhaled AAT restored protease anti-protease homeostasis and reduced the percentage of neutrophils and NE concentration in the lower respiratory tract of AAT deficient individuals. Detection of normal AAT in the plasma of study subjects indicates that inhaled AAT passed from the alveolar compartment and the interstitial space. Based on these findings inhaled AAT may be an effective and safe preventive therapy for the prevention of lung disease in AAT deficient individuals.

Example 2: The Inhalation of AAT Significantly Increased the Levels of AAT, AAT Complex and ANEC in Subjects at Early Stages of the Disease (with FEV1% of Predicted ≥80%)

Methods:

For each subject with FEV1% of predicted ≥80% a change from baseline of the parameters was calculated. Descriptive statistics of Number of subject, mean, Standard Deviation, median, minimum and maximum were calculated. Non-parametric ANOVA approach to test for differences between treatment groups were applied using Kruskal-Wallis test, and p-values adjusted for multiple comparisons was calculated (FDR p-values).

Results:

The numbers of subjects in the subgroup of subjects with FEV1% of predicted ≥80% are 5, 7 and 4 subjects in Placebo, 80 mg and 160 mg, respectively. As shown in Table 1, significant finding were demonstrated in Average AAT, AAT complex, and ANEC.

The median AAT in 160 mg and 80 mg treatment groups were higher than placebo, 10 nmol versus 4017 nmol and 16,596 nmol respectively p-value=0.0014; the median AAT complex in 160 mg and 80 mg treatment groups were higher than placebo, 227 nmol versus 38 nmol and 0 nmol respectively p-value=0.0062; and median ANEC in 160 mg and 80 mg treatment groups were higher than placebo, 266 nmol versus 2273 nmol and −96 nmol respectively p-value=0.0057.

TABLE 1

Descriptive Statistics-non-parametric ANOVA for differences between groups

| Parameter | Actual Daily Treatment | N | Mean (SD) | Median (min., max.) | P value Kruskal Wallis | P value FDR corrected |
|---|---|---|---|---|---|---|
| Average Alpha-1 Antitrypsin (nM) | 160 mg AAT | 4 | 27555.77 (29417.87) | 16596.55 (6122.02, 70907.95) | 0.0014 | 0.0200 |
| | 80 mg AAT | 7 | 3765.01 (1691.35) | 4017.01 (1803.77, 5870.77) | | |
| | Placebo | 5 | 92.06 (162.15) | 10.09 (−53.54, 337.95) | | |
| Average Alpha-1 Antitrypsin Neutrophil Elastase (complex, nM) | 160 mg AAT | 4 | 358.33 (450.75) | 226.98 (13.83, 965.53) | 0.0062 | 0.0291 |
| | 80 mg AAT | 7 | 30.20 (22.45) | 38.48 (5.87, 67.36) | | |
| | Placebo | 5 | −0.47 (0.92) | 0.00 (−2.03, 0.22) | | |
| Average Anti-Neutrophil Elastase Capacity (ANEC, nM) | 160 mg AAT | 4 | 9002.78 (6907.99) | 7635.72 (2242.31, 18497.35) | 0.0057 | 0.0291 |
| | 80 mg AAT | 7 | 1978.69 (1279.31) | 2273.62 (178.77, 3800.35) | | |
| | Placebo | 5 | −442.57 (1095.46) | −96.12 (−1980.72, 884.27) | | |
| Average Neutrophil Elastase (nM) | 160 mg AAT | 4 | −182.06 (390.77) | −40.46 (−757.87, 110.56) | 0.8771 | 0.9831 |
| | 80 mg AAT | 7 | −80.16 (112.03) | −53.21 (−318.66, 20.22) | | |
| | Placebo | 5 | −243.99 (566.28) | −244.59 (−974.62, 535.15) | | |

Example 3: Effect of AAT Early Intervention Treatment on Elastase-Induced Chronic COPD Model in Mice The aim of this study was to test the effect of AAT as an early intervention treatment in elastase-induced chronic COPD model in mice.

Principle of the Test:

The principle of the test is based on the induction of COPD by intratracheal instillation of elastase once a week for four weeks, with or without prophylactic AAT treatment in the day previous to the elastase instillation. The feasibility of the COPD model in mice using intratracheal instillation of porcine pancreatic elastase (PPE) was tested in a previous pilot study with 6 mice and results were compared to 2 control mice. PPE treatment was shown to induce alveolar destruction in lungs of mice, while saline treatment did not affect the lungs.

Experimental Procedure

Two groups of mice, each with 15 Females C57BL/6J mice (20-25 g, 10 weeks of age) were randomly assigned.

Group A (treated with AAT): mice were anesthetized and received intra-tracheal instillation of 20 μl of AAT 2% (a sterile, ready to use, solution which is provided as four single-use vials in 20 mM sodium phosphate containing 0.7% NaCl): four instillations at 1-week intervals. 24 hours post each AAT 2% instillation, an instillation of 0.2 U of PPE in 20 μl of saline was received. At the end of week 2, 3, 4 (a week after the $2^{nd}$, $3^{rd}$ and $4^{th}$ treatments, respectively), 5 mice were sacrificed and their lungs were assessed histologically.

Group B (control): mice were anesthetized and received intra-tracheal instillation of 20 μl of saline: four instillations at 1-week intervals. 24 hours post each saline instillation; an instillation of 0.2 U of porcine pancreatic elastase (PPE, Sigma) in 20 μl of saline was received. At the end of week 2, 3, 4 (a week after the $2^{nd}$, $3^{rd}$ and $4^{th}$ treatments, respectively), 5 mice were sacrificed and their lungs were assessed histologically.

Tests and Evaluations

Morbidity and mortality check were performed during the acclimation phase and study. There were no abnormalities or death during the study.

Body weight and food consumption were recorded during acclimation and before test items administration.

Collection of Blood Samples:

At the end of week 2, 3, 4 (a week after the 2nd, 3rd and 4th treatments), 5 mice from each group were kept under light anesthesia with isoflurane. 400 microliters of blood were collected from the retro-orbital sinus into tubes and the tubes were kept in room temperature. Tubes were centrifuged for 10 minutes at 14000 rpm at 4° C. and about 200 microliters of serum were harvested and stored at −80° C.

Organ/Tissue Collection & Fixations

Anesthetized mice were sacrificed for lung histology. The necks and the trachea were exposed, a needle was inserted through the trachea, and the lungs were internally fixed in 4% Formaldehyde using the gravitation method.

Longitudinal cross sections were performed on each lung. All tissues were trimmed into block cassettes.

Slides Preparation

Tissues were trimmed, embedded in paraffin, sectioned at no more than 5 microns thickness, and stained with Hematoxylin & Eosin (H&E). The histological processing (embedding and sectioning of tissues, followed by preparation and staining of the slides) was performed by CDX-Diagnostics, Jerusalem, Israel).

Microscope Photography Method and Histological Evaluation

Pictures were taken using an Olympus BX60 microscope at ×40 magnification. All slides were stained with H&E and scored for apparent signs of emphysema by one pathologist blinded to treatment.

Digital Image Analysis:

Image analysis was performed using "Image Pro Plus" Ver 6.3, by Media Cybernetics, US. From each histological slide four histologic pictures were performed and sent for a digital analysis using a ×40 magnification.

Protocol:

Spatial calibration was applied (marked calibration bar in the image).

Area of Interest (AOI) selection was applied.

Threshold selected, based on HSI color system, Hue, Saturation and Intensity, The measurement of area was conducted by pixels counting.

Intensity between 96 to 255 levels was depicted to show only the void spaces.

The calibrated parameters, "Area" and "Perimeter3" were measured and used for creating the statistical data.

Results

Histopathological Description

Lung from animals of groups A (treated) and B (control) were harvested in three different time intervals with a week time in between them.

Group A (treated): showed an average of respectively 6.39, 9.48 and 12.15 Area/Perimeter$^3$ mean of alveolar spaces.

Group B (control): showed an average of respectively 10.88, 15.88 and 15.50 Area/Perimeter3 mean of alveolar spaces.

Figure 4:
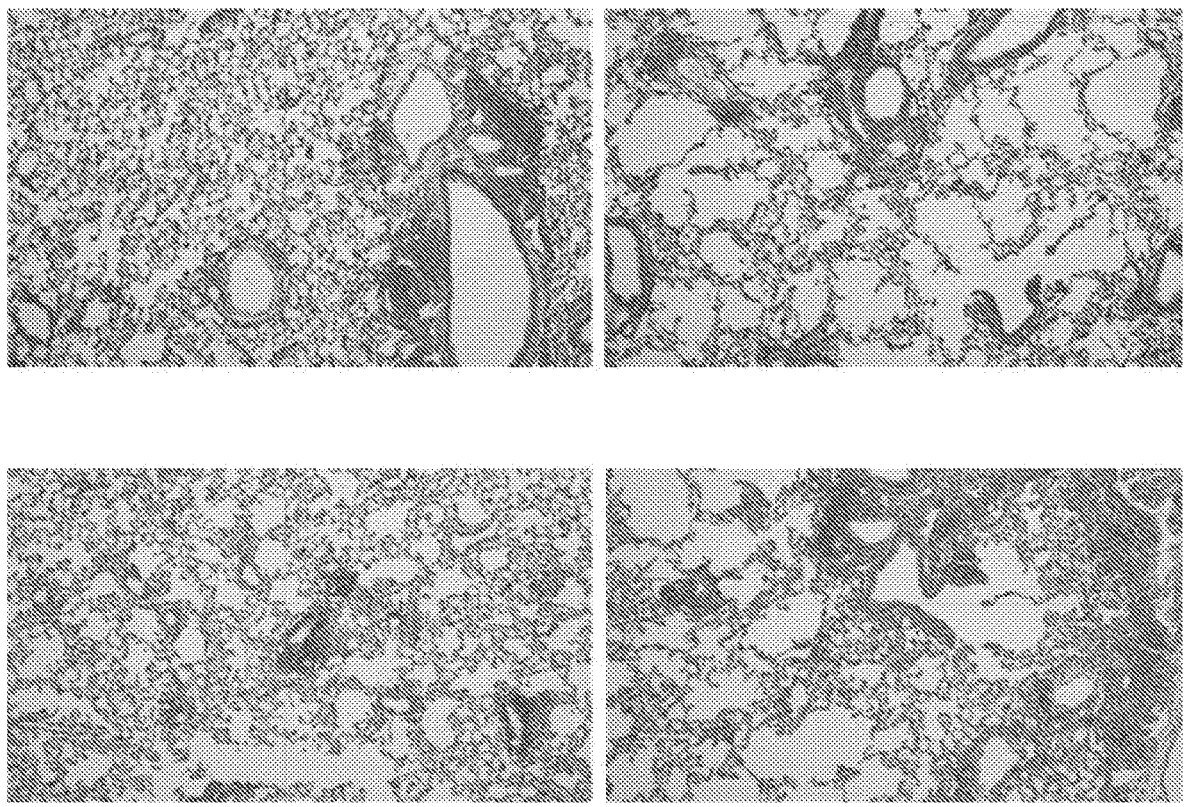
FIG. 4 shows representative photographs of slices of the lungs obtained from elastase-induced chronic COPD mice model, sacrificed after 2 weeks. Left row are representatives from group A (AAT treated) and in the right row group B (control), ×40 H&E.
Figure 5A:
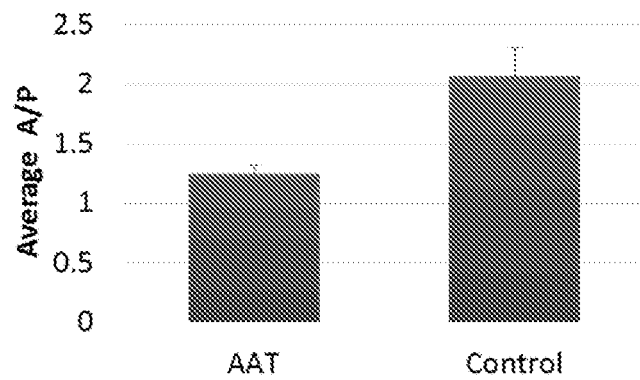
FIG. 5A demonstrates the average of Area/perimeter ratio (high value=>larger gaps) after 2 weeks of treatment with AAT, followed by exposure to Elastase as compared to control.
Figure 5B:
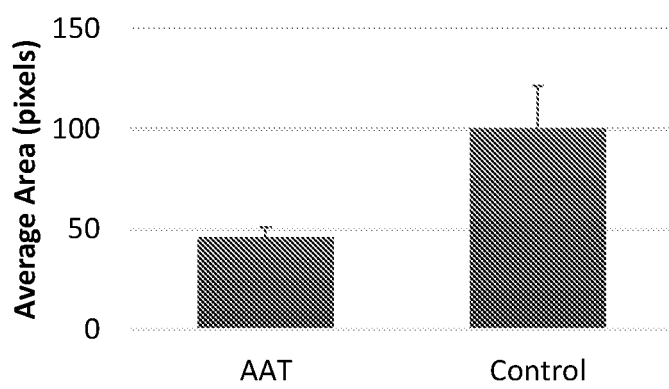
FIG. 5B demonstrates the average "air" area after 2 weeks of AAT treatment followed by exposure to Elastase as compared to control.

Representative photographs of slices of the lungs obtained from elastase-induced chronic COPD mice model, sacrificed after 2 weeks are shown in FIG. 4. Left row are representatives from group A (AAT treated) and in the right row group B (control), ×40 H&E. FIG. 5A demonstrates the average of Area/perimeter ratio (high value=>larger gaps) after 2 weeks of treatment with AAT, followed by exposure to Elastase as compared to control. FIG. 5B demonstrates the average "air" area after 2 weeks of AAT treatment followed by exposure to Elastase as compared to control.

Figure 6:
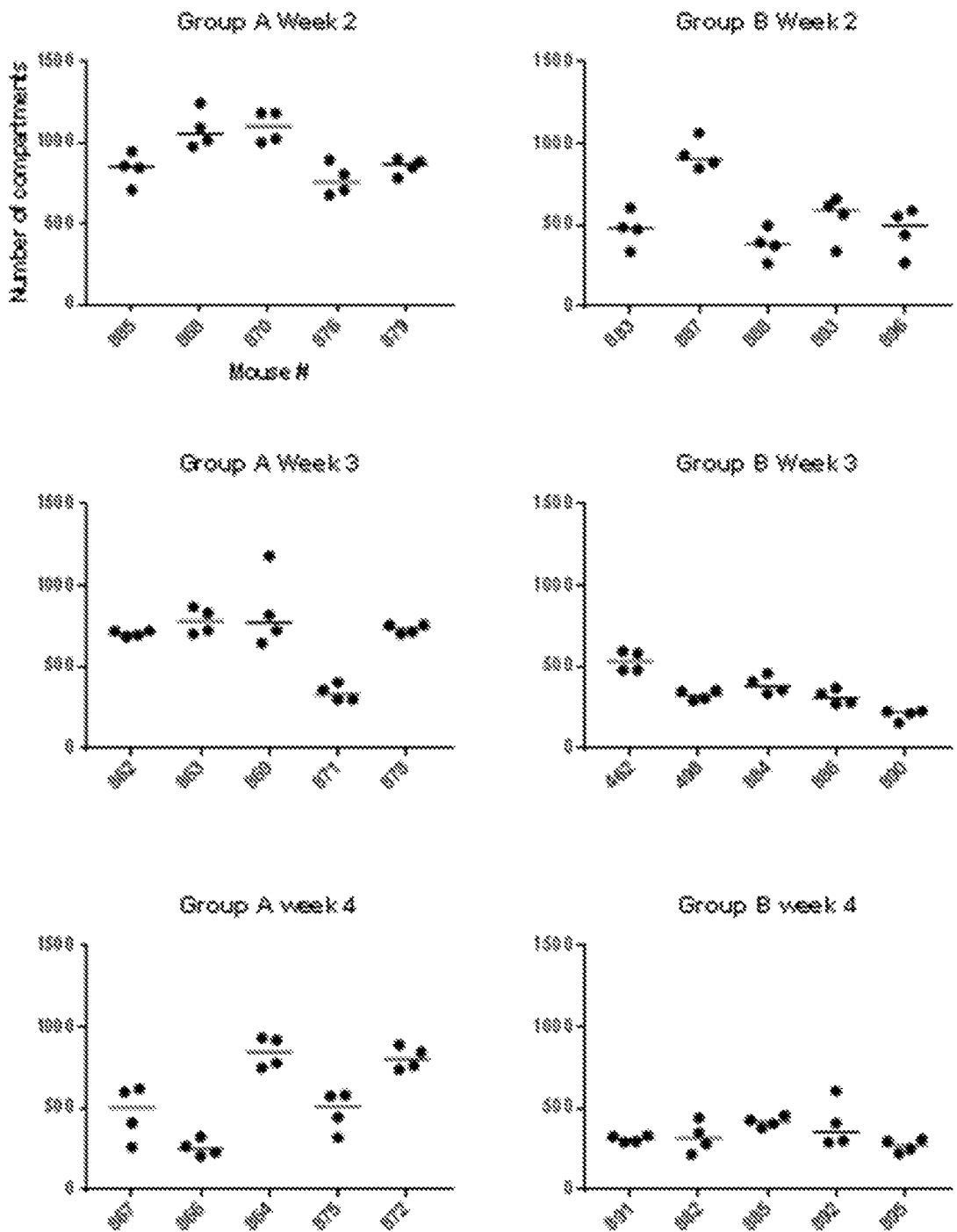
FIG. 6 demonstrates the number of airspaces per field in slices of the lungs obtained from elastase-induced chronic COPD mice model. Group A (AAT treated) and group B (control).

FIG. 6 demonstrates the number of airspaces per field in slices of the lungs obtained from elastase-induced chronic COPD mice model. Group A (AAT treated) and group B (control). Reduction of the number of airspaces per field is correlated with alveolar distraction and severe lung damage.

The results emphasize that AAT intra-tracheal instillation ameliorates elastase-induced pulmonary emphysema in mice and support the use of AAT administration via inhalation for early intervention and prevention of the progression of pulmonary diseases.

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed functions may take a variety of alternative forms without departing from the invention.

The invention claimed is:

1. A method for preventing the progression of a pulmonary disease in a subject in need thereof, comprising administering to the subject, a therapeutically effective amount of alpha 1-antitrypsin (AAT) via inhalation, wherein the subject has alpha 1-antitrypsin deficiency and a lung function measurement of Forced expiratory volume in 1 second $(FEV_1) \geq 80\%$ of predicted post-bronchodilator indicating that the pulmonary disease is at early stages of the disease.

2. The method of claim 1, wherein the pulmonary disease is selected from the group consisting of small airway disease, chronic bronchitis, emphysema, chronic obstructive pulmonary disease (COPD), cystic fibrosis, bronchiectasis, asthma, pneumonia, parenchymatic and fibrotic lung diseases or disorders, interstitial pulmonary fibrosis, and sarcoidosis.

3. The method of claim 1, wherein the AAT is naturally occurring AAT purified from an unpurified mixture of proteins by a process comprising chromatography on a plurality of ion exchange resins; comprising a first anion exchange resin followed by a cation and a second anion exchange resins.

4. The method of claim 1, wherein the subject is selected from the group consisting of a pre-pubertal child, a pre-pubertal adolescent, an adolescent and an adult.

5. The method of claim 1, wherein the therapeutically effective amount of AAT is about 10 mg to about 250 mg AAT per day.

6. The method of claim 1, wherein the therapeutically effective amount of AAT is about 80 mg to about 160 mg AAT per day.

7. The method of claim 1, wherein the therapeutically effective amount of AAT is about 0.2 mg/kg/day to about 15 mg/kg/day.

8. The method of claim 1, wherein the AAT is aerosolized.

9. The method of claim 1, wherein the AAT is administered using a nebulizer.

10. The method of claim 1, wherein the AAT is administered at least once per day.

11. The method of claim 1, wherein the subject is diagnosed by lung computed chest tomography.

12. The method of claim 1, wherein the AAT is recombinant or transgenic.

13. The method of claim 1, wherein said administering the AAT results in at least one of reduced hospitalization; reduced intensive care or mechanical ventilation need; reduced healthcare utilization or burden; reduced absences from school or work; decreased antibiotic need; decreased steroid need; decreased relapse frequency; and, decreased morbidity.

14. The method of claim 1, wherein the pulmonary disease is cystic fibrosis in a pre-pubertal subject.

15. The method of claim 1, wherein said administering the AAT results in at least one-fold increase of AAT in epithelial lining fluid.

16. The method of claim 15, wherein said administering the AAT results in at least two-fold increase of AAT in the epithelial lining fluid.

17. The method of claim 1, wherein said administering the AAT results in at least one-fold increase of AAT-Neutrophil Elastase (AAT-NE) complex in epithelial lining fluid.

18. The method of claim 17, wherein said administering the AAT results in at least two-fold increase of AAT-NE complex in the epithelial lining fluid.

19. The method of claim 1, wherein said preventing the progression of the pulmonary disease comprises preventing increase in NE level in epithelial lining fluid.

\* \* \* \* \*